US00PP11006P

United States Patent [19]

Danziger

[11] Patent Number: Plant 11,006

[45] Date of Patent: Jul. 13, 1999

[54] PETUNIA PLANT NAMED 'DANCASBLUE'

[75] Inventor: Gabriel Danziger, Nir Zvi, Israel

[73] Assignee: Danziger - "Dan" Flower Farm, Post Beit Dagan, Israel

[21] Appl. No.: 08/865,875

[22] Filed: May 30, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS 5,523,520 6/1996 Hunsperger ..... 800/200

*Primary Examiner*—Howard J. Locker

*Attorney, Agent, or Firm*—Foley & Lardner

[57] ABSTRACT

The petunia plant named 'Dancasblue' is particularly characterized by light blue main flower color, with dark purple veins and throat, strong and spreading growth habit, flowering above the foliage, and its good winter performance.

2 Drawing Sheets

The present invention comprises a new and distinct cultivar of petunia, known by the cultivar name 'Dancasblue'.

'Dancasblue' was originated from a hybridization made by the inventor, Gabriel Danziger, in a controlled breeding program in Mishmar Hashiva, Israel in 1996. The male and female parents were unnamed proprietary lines used in the breeding program.

'Dancasblue' was discovered and selected as one flowering plant within the progeny of the stated cross by the inventor Gabriel Danziger in May 1996 in a controlled environment in Mishmar Hashiva, Israel.

The first act of asexual reproduction of 'Dancasblue' was accomplished when vegetative cuttings were taken from the initial selection in June 1996 in a controlled environment in Mishmar Hashiva by a technician working under the supervision of the inventor. Horticultural examination of selected units was initiated in September 1996 and has demonstrated that the combination of characteristics as herein disclosed for 'Dancasblue' are firmly fixed and are retained through successive generations of asexual reproduction.

'Dancasblue' has not been observed under all possible environmental conditions. The phenotype may vary somewhat with variations in environment such as temperature, light intensity and day length, without any variations in genotype. The following observations, measurements and comparisons describe the plants grown in Mishmar Hashiva under greenhouse conditions which approximate those generally used in commercial practice.

The following traits have been repeatedly observed and are determined to be basic characteristics of 'Dancasblue' which in combination distinguish this petunia as a new and distinct cultivar:

1. Strong and spreading growth habit.
2. Intense light blue flower color.
3. Dark green, smooth, rounded foliage.
4. Performs well during winter in warmer climates such as Israel.
5. Suitable for containers and as a bedding plant.
6. Flowers rise above the foliage.

Of the many commercial cultivars known to the inventor, the most similar in comparison to 'Dancasblue' is the commercial cultivar 'Surfinia Blue Vein'. In comparison to 'Surfinia Blue Vein', the cultivar 'Dancasblue' has better performance during winter, better growth habit and flowering, its flowers rise more prominently above the foliage, and its flower color is a more intense blue. Further, the internodes of 'Dancasblue' are longer and less branched.

While the cultivar name of this plant is 'Dancasblue' for purposes of international recognition, it is being marketed in the United States under the tradename "Blue Spark".

In the accompanying photographic drawings, Sheet 1 comprises a side view showing typical flower and foliage characteristics of 'Dancasblue', with the color being as true as possible with illustrations of this type.

Sheet 2 is a close-up view showing the corolla throat and flower vein details.

In the following description color references are made to The Royal Horticultural Society Colour Chart. The color values were determined between 10:00–12:00 a.m. in January 1997 under full sunlight at Mishmar Hashiva, Israel.

Classification:

*Botanical.*—Petunia hybrida.

*Commercial.*—Petunia cultivar 'Dancasblue'.

Plant:

*Growth habit.*—Vigorous, trailing.

*Plant height.*—Approximately 15–21 cm.

*Spreading area.*—Approximately 115–128 cm.

*Blooming period.*—All year round.

*Branching.*—Trailing growth habit, free, densely branched plant.

*Pinching.*—Pinching is required early in growth to induce a branched plant. Pinching generally delays the first flowering; however, after the initial pinching, flowering is fast and free with no additional pinching required.

Stem:

*Thickness.*—2–3 mm.

*Color.*—Green, R.H.S. 138A.

*Pubescence.*—Yes.

*Branching.*—Free, after initial pinching; five (5) plants per container are needed to obtain branching as illustrated in photographic drawing Sheet 1.

*Length of internode.*—35–40 mm.

*Rooting.*—Stems, while attached to the plant, do not root at the nodes when placed in moist soil. Cuttings do root.

Leaves:

*Arrangement on stem.*—Alternate.

*Shape.*—Ovate.

*Size.*—Approximately 5 cm.

*Thickness.*—2 mm.

*Color.*—Dark green; upper surface R.H.S. 137A.

*Pubescence.*—Present.

Flowers:

*Orientation at opening.*—Upright.

*Type.*—Single.

*Shape.*—Regular rounded corolla united with 5 lobes along straight tube about 50 mm in length.

*Diameter.*—45 mm.

*Color.*—Upper surface: Main color light blue R.H.S. 91C with veins and tubular throat being an intense dark violet R.H.S. 83A. Lower surface: Similar to upper surface, but colors are slightly lighter, more pale.

*Calyx.*—Five pubescent sepals, about 12 mm in length, coloration is green (closest to R.H.S. 138A).

*Peduncle.*—Length: 30–35 mm. Color. Green.

*Reproductive organs.*—Pistil: Number: 1. Color: Light green. Stamens: Number: 5. Anther: Gray-blue. Filiament: White.

*Other characteristics.*—The cultivar sets thousands of seeds in a full-grown plant.

Disease resistance: The new cultivar is highly resistant to rain, heat and drought, and has to date shown no unusual susceptibility to disease so common to this species.

I claim:

1. A new and distinct cultivar of petunia plant named 'Dancasblue' as herein shown and described.

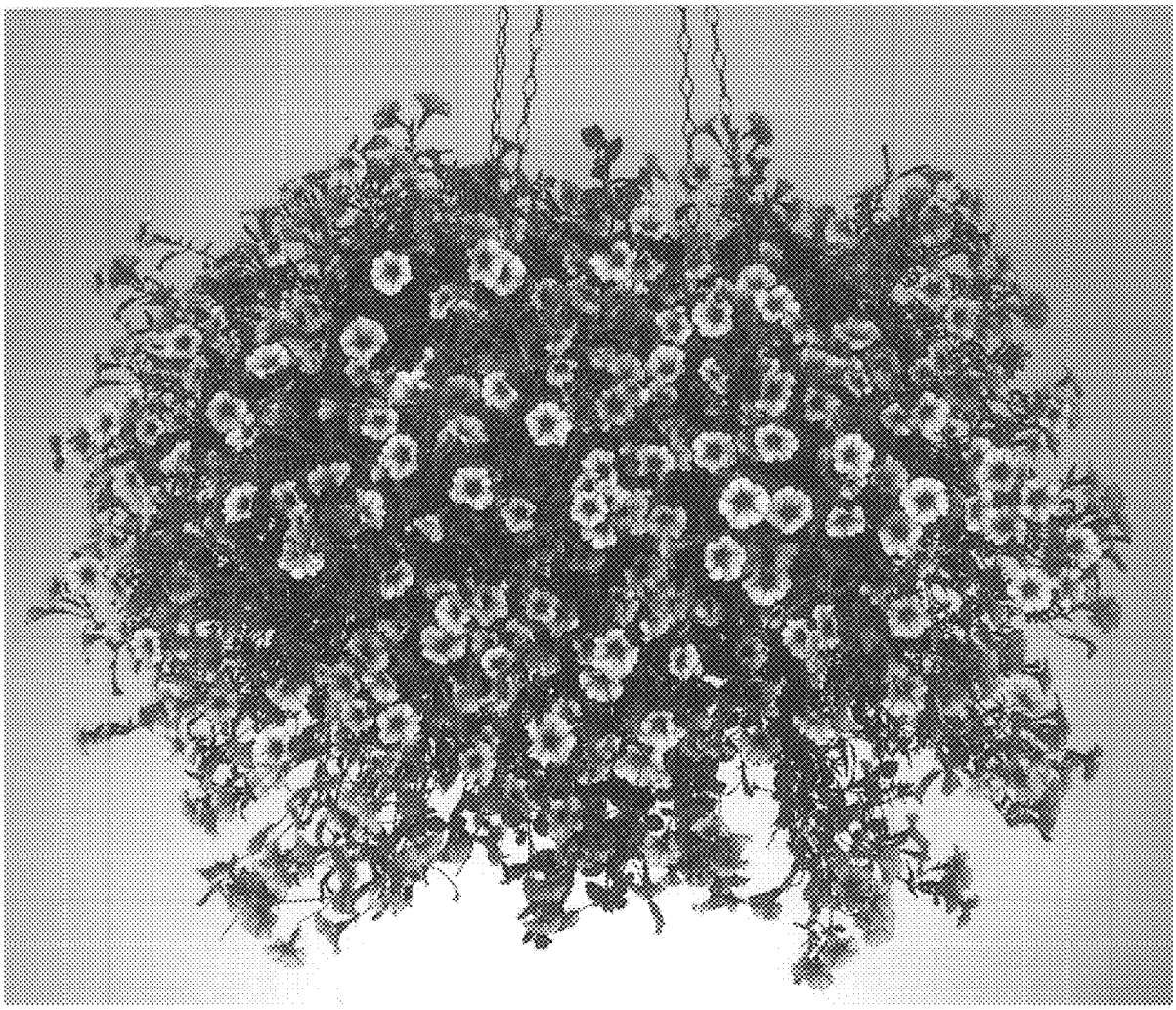

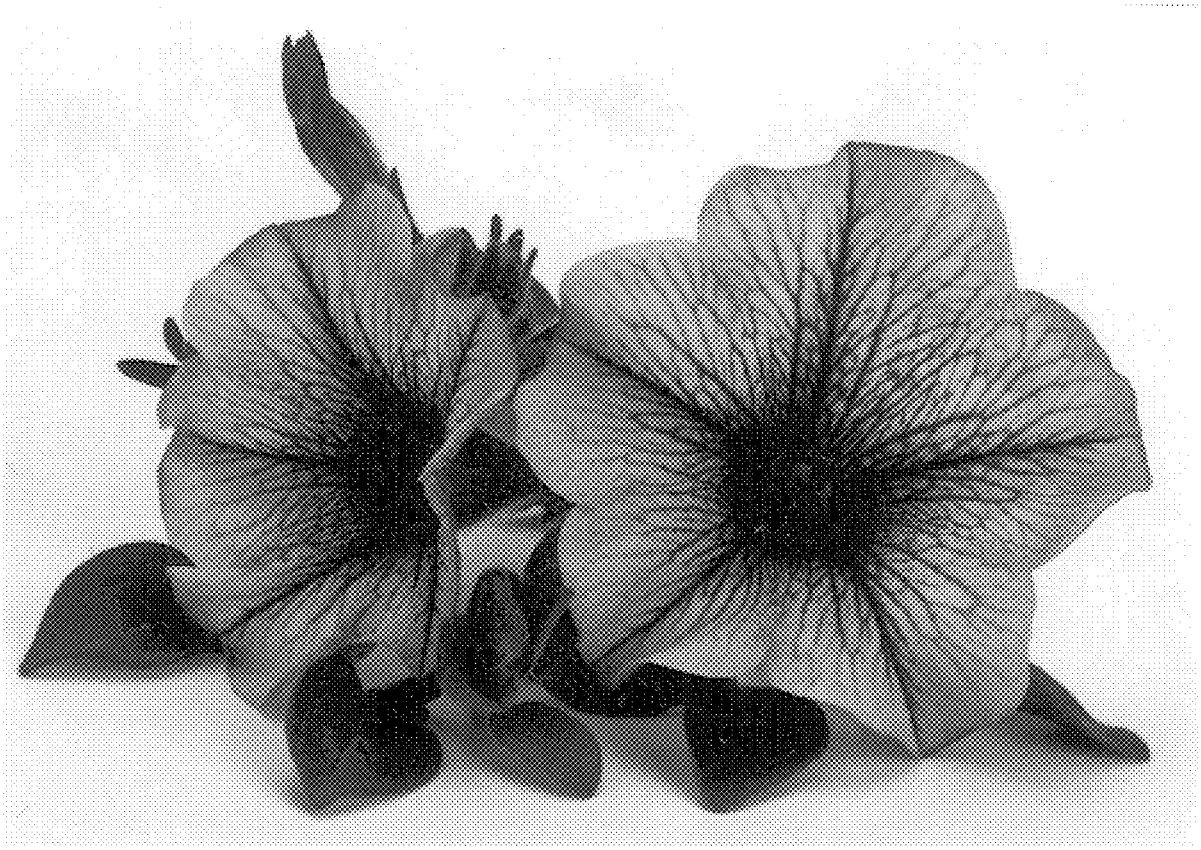

* * * * *